United States Patent [19]

Ishida

[11] 4,380,466

[45] Apr. 19, 1983

[54] HEXAHYDROISOINDOLE DERIVATIVES, AND THEIR PRODUCTION AND USE

[75] Inventor: Yasuo Ishida, Suita, Japan

[73] Assignee: Takeda Chemical Industries, Ltd., Osaka, Japan

[21] Appl. No.: 265,410

[22] Filed: May 20, 1981

[30] Foreign Application Priority Data

May 26, 1980 [JP] Japan .................................. 55-70478

[51] Int. Cl.³ .................... A01N 43/38; C07D 209/46
[52] U.S. Cl. .......................................... 71/96; 548/476
[58] Field of Search ......... 71/96; 260/326 S, 326 HL, 260/325 PH; 548/476

[56] References Cited

U.S. PATENT DOCUMENTS 4,001,272  1/1977  Goddard ................................. 71/96

FOREIGN PATENT DOCUMENTS 50-148529  11/1975  Japan ............................. 260/326 S Primary Examiner—Donald G. Daus
Assistant Examiner—M. C. Eakin
Attorney, Agent, or Firm—Burgess, Ryan and Wayne

[57] ABSTRACT

A novel hexahydroisoindole derivative of the formula,

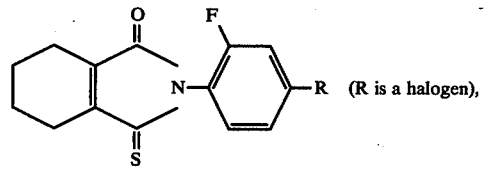

(R is a halogen), which can be produced by dehydration of the corresponding 3a-hydroxy-octahydroisioindole derivative or by reaction of the corresponding 3-chloro-hexahydroisoindole with a thiol sulfonate.

The derivative is useful as an intermediate for producing a compound having a substituted or unsubstituted thiol group at 3-position and can be utilized as a herbicide possessing low toxicity to crops and animal.

10 Claims, No Drawings

HEXAHYDROISOINDOLE DERIVATIVES, AND THEIR PRODUCTION AND USE

The present invention relates to novel hexahydroisoindole derivatives of the formula:

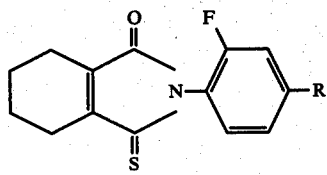

wherein R is a halogen, to processes for producing the same, and to herbicides containing said derivative (I). More particularly, the invention relates to:

(1) a hexahydroisoindole derivative of the formula (I)
(2) a process for producing a compound of the formula (I), which comprises subjecting to dehydration a compound of the formula:

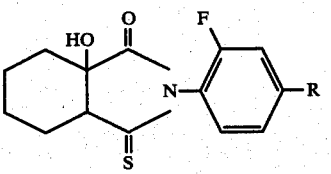

wherein R is as defined above.
(3) a process for producing a compound of the formula (I) which comprises reacting a compound of the formula:

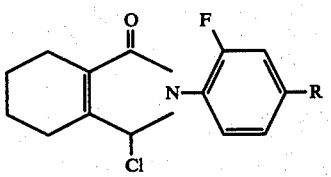

wherein R is as defined as above, with a thiol sulfonate: and
(4) herbicides containing as an active ingredient a hexahydroisoindole derivative of the formula (I).

As the halogen represented by R in each of the above-mentioned formulas, use is made of fluorine, chlorine, bromine and iodine.

A large number of chemical agents have been so far utilized as herbicides, but very few have been satisfactory in terms of herbicidal effect against weeds, phytotoxicity to crops, toxicities to man and animals and fishes and shellfishes, environment pollution, etc.

The present inventor, after continued extensive research with a specific view to resolving such problems, found that the above-mentioned compound (I) posesses strong herbicidal activity and less phytotoxicity, and the finding, followed by additional investigation, has led to the completion of the present invention. Thus, the above-mentioned novel compound (I) not only posseses excellent weedkilling action against a wide range of weeds such as paddyfield weeds, e.g. Barnyardgrass (*Echinocholoa oryzicola Vasing*), Tamagayatsuri (*Cyperus difformis L.*), Konagi (*Monochoria vaginalis Presl.*), Azena (*Lindernia procumbens Philcox*), Kikashigusa (*Rotala indica Koehne*) and Spike rush (*Eleocharis acicularis Roem et Schult*), and field weeds, e.g., crabgrass (*Digitaria adsendens Henr.*), Pigweed (*Amaranthus retroflexus L.*), Lamb's-quaters (*Chenopodium album L. var. centrorubrum Makino*), Inutade (*Polygonum Blumei Meisn.*), common purslane (*Portulaca oleraccea L.*) and Green foxtail (*Setaria viridic Blauv.*), but also exhibits remarkably high selectivity for some crops such as leguminous plants, e.g. soybean, and cotton, when it is applied by the pre-emergence soil treatment. In addition, the compound (I) can be said to be the chemical agents which can be safely utilized from the standpoint of toxicity and environmental pollution.

The hexahydroisoindole derivative (I) can be produced by reacting a compound of the general formula (III) with hydrogen cyanide to give a compound of the general formula:

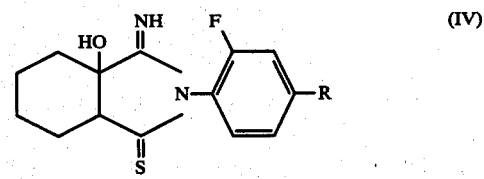

which is hydrolyzed to a compound of the general formula (II), followed by subjecting to a dehydration reaction. The starting compound (III) utilized herein is novel compound, and can be produced, for example, in accordance with the procedure described in Chemische Berichte, vol. 95, pp. 926 (1962) or Liebigs Annalen der Chemie, vol. 673, pp. 132 (1964), as shown by the following equation.

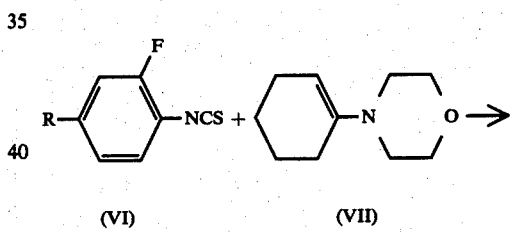

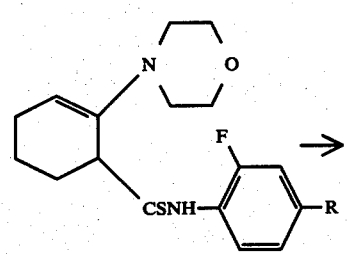

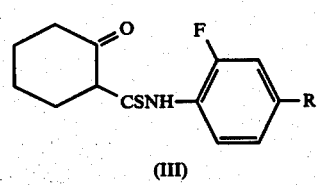

(wherein R is as defined above).
The compound (VIII) obtained by the reaction between the compounds (VI) and (VII) in the above-described reaction equation can be isolated and purified by the procedures known per se, but can also be derived into the compound (III) directly without isolation and purification. In the reaction between the compound (III) and hydrogen cyanide, hydrogen cyanide may be utilized in any form of gaseous hydrogen cyanide, salts with alkali metals such as sodium cyanide and potassium cyanide or cyanhydrins such as acetone cyanhydrin.

In the case of sodium cyanide or potassium cyanide being utilized, generally, the reaction is carried out in the coexistence of a mineral acid such as hydrochloric acid, phosphoric acid and sulfuric acid, organic acid such as acetic acid, or ammonium chloride, etc. In cases in which acetone cyanhydrin is used, normally, the reaction is conducted in the presence of a base, e.g. sodium carbonate and potassium carbonate, as a catalyst.

As the reaction solvent, use is made of toluene, dichloromethane, chroloform, ether, tetrahydrofuran, dioxane, acetonitrile, methanol, ethanol, water, etc. The reaction temperature is not specifically restricted, and the reaction is conducted preferably at 0° to 80° C. The compound (IV) thus obtained can be isolated by the procedures known per se, but can also be advantageously derived into the compound (II) by directly hydrolyzing in the reaction solution without isolating. The hydrolysis of the compound (IV) is advantageously conducted in the presence of a mineral acid such as hydrochloric acid, phosphoric acid and sulfuric acid, or silica gel, etc.

The dehydration reaction of the compound (II) into the compound (I) is advantageously carried out by reacting the compound (II) with for example an acid anhydride or acid halide, whereby it is recommended to allow bases, such as tertiary amines, e.g., pyridine, quinoline, dimethylaniline and triethylamine, alkali metal carbonates e.g. sodium carbonate and potassium carbonate, and fatty acid salts with alkali metals e.g. sodium acetate, to coexist. As the acid anhydride, use is made of acetic anhydride, propionic anhydride, trichloroacetic anhydride, trifluoroacetic anhydride, etc., while, as the acid halide, use is made of benzoyl chloride, ethyl chlorocarbonate, thionyl chloride, thionyl bromide, phosphorus oxychloride, etc. As the favorable combination of the base and the acid anhydride or acid halide, use is made of acetic anhydride and pyridine, trifluoroacetic anhydride and pyridine, thionyl chloride and pyridine, and the like. As the reaction solvent, normally, use is made of for example toluene, dichloromethane, chroloform, carbon tetracholoride, diethyl ether, tetrahydrofuran, dioxane, ethyl acetate, acetone, acetonitrile, pyridine, etc. The reaction temperature is not specifically restricted, and the reaction is conducted at 0° to 120° C., preferably 0° to 80° C.

The compound (I) can also be produced by reacting a compound of the general formula (V) with a thiol sulfonate. The thiol sulfonate is represented, for example, by the general formula, $R_1SO_2SR_2$ (wherein $R_1$ is a lower alkyl group ($C_1$-$C_4$) such as methyl, ethyl, propyl, and butyl, and an aryl group such as phenyl and naphthyl, whereby the aryl group may be substituted by straight-chain or branched lower alkyl groups ($C_1$-$C_4$) such as methyl, ethyl, propyl and i-propyl, lower alkoxy groups such as methoxy and ethoxy, nitro group, and halogen such as fluorine, chlorine, bromine and iodine; $R_2$ is an alkali metal such as sodium and potassium, an alkaline earth metal such as calcium, and trialkyl ($C_1$-$C_4$) ammonium such as trimethyl ammonium and triethyl ammonium). Any solvent may be an inert solvent such as toluene, dichloromethane, chloroform, carbon tetrachloride, diethyl ether, tetrahydrofuran, dioxane, ethyl acetate, acetone, acetonitrile, dimethylformamide, etc. may be utilized. The reaction may be conducted at room temperature or under heating, preferably at 10° to 100° C.

The starting compound (V) can be produced, for example, by the procedure as shown by the equation.

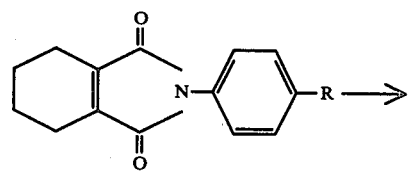

(IX)

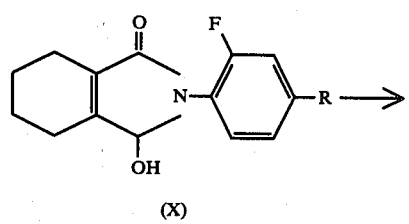

(X)

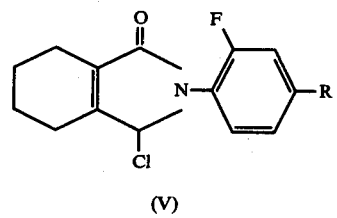

(V)

(wherein R is as defined above).

Thus, in accordance with the procedure described in Journal of Organic Chemistry, vol. 26, pp. 2273 (1961), the compound (IX) is reduced with sodium borohydride to give the compound (X), which is then reacted with thionyl chloride, thereby affording the compound (V) in high yields.

The compound (I) can also be produced by the procedure known per se which comprises reacting the tetrahydrophthalimide derivative (IX) with for example phosphorus pentasulfide. As the reaction solvent, frequent use is made of aromatic hydrocarbons such as benzene, toluene and xylene, pyridine, carbon disulfide, etc. The reaction is conducted at room temperature or under warming, but is normally carried out advantageously in the neighborhood of the boiling point of a solvent used.

The compounds (I) thus obtained can be isolated and purified by procedures known per se such as concentration, concentration under reduced pressure, solvent extraction, phasic transfer, crystallization, recrystallization and chromatographic separation.

In utilizing the compound (I) of the present invention as herbicides, one or not less than two kinds of the compound (I), depending upon the application purpose, are dissolved, or suspended, in a suitable liquid carrier (for example, solvent) or are mixed with, or adsorbed on, an appropriate solid carrier (for example, diluent, dust-diluent), followed by adding emulsifiers, suspending agents, spreaders, penetrants, wetting agents, thickening agents, stabilizers, etc., if necessary, to thereby apply in the preparation forms such as oil-borne preparations, emulsifiable concentrates, wettable powders, dusts, granules, tablets, sprays and ointments. Such preparations can be prepared by the procedures known per se.

The proportion in which the active ingredient is contained in the herbicides varies with the intended application purpose, but is suitably in the range of 10 to 90 weight % for emulsifiable concentrates, wettable powders, etc., appropriately in the region of 0.1 to 10 weight % for oil-borne preparations, dusts, etc., and properly in the range of 1 to 20 weight % for granules, although such concentrations may be conveniently changed with the intended application purpose.

Emulsifiable concentrates, wettable powders, etc. may better be sprayed after diluting and extending suitably with water, etc. (for example, 100 to 100,000 times) on the occasion of application.

Suitable examples of the liquid carrier (solvent) which is used in the herbicide include solvents such as water, alcohols (e.g., methyl alcohol, ethyl alcohol, ethylene glycol, etc.), ketones (e.g., acetone, methyl ethyl ketone, etc.), ethers (e.g., dioxane, tetrahydrofuran, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.) and other halogenated hydrocarbons (e.g., chloroform, carbon tetrachloride, etc.) acid amides (e.g., dimethylformamide), esters (e.g. ethyl acetate, butyl acetate, glycerine esters of fatty acids, etc.) and nitriles (e.g., acetonitrile), and not only one kind of these solvents but mixtures of not less than two kinds of these are utilized. As the solid carrier (diluent, dust-diluent), use is made of vegetable powders (e.g., soybeans meal, tabaco meal, wheat flour, wood flour, etc.), mineral powders (e.g., clays such as kaolin, bentonite and acid clay, talc such as talc powder and azalmatolite powder silicas such as diatomaceous earth and mica powder, etc.), alumina, sulfur powder, activated charcoal and the like, and one of or mixtures of not less than two kinds of these are utilized.

As the ointment base, suitably selected can be one or not less than two kinds of polyethylene glycol, pectin, polyhydric alcohol esters of higher fatty acids such as glycerine monostearate, cellulose derivatives such as methylcellulose, sodium arginate, bentonite, higher alcohols, polyhydric alcohols such as glycerine, petrolatum, white petrolatum, liquid paraffin, lard, various kinds of vegetable oils, lanolin, lanolin anhydricum, hardened oil, waxes, resins, etc., either solely or added with various surfactants and others.

As the surfactants which are used as emulsifiers, spreaders, penetrants, dispersing agents, etc., use is made of soaps, polyoxyalkyl aryl esters (e.g., Nonal ®) produced by Takemoto Oils & Fats Co., Japan), alkyl sulfates (e.g. Emal 10 ®, Emal 40 ®, etc. produced by Kao Atlas Co., Japan), alkyl sulfonate (e.g., Neogen ®, Neogen T ®, etc. produced by Dai-ichi Kogyo Seiyaku Co., Japan; Neopelex ®, produced by Kao Atlas Co., Japan), polyethylene glycol ethers (e.g., Nonipol 85 ®, Nonipol 100 ®, Nonipol 160 ®, etc. produced by Sanyo Chemical Industries, Japan), polyhydric alcohol esters (e.g. Tween 20 ®, Tween 80 ®, etc. produced by Kao Atlas Co., Japan) etc., if necessary.

In utilizing the compound (I) as herbicides, their application amount is about 1 to 50 g, preferably about 2 to 40 g per are of a paddy field, and about 1 to 50 g, preferably about 2 to 40 g, per are of plowed field. In addition, it is suitable to use the compound (I) as a pre-emergence treatment agent. The compound (I) shows lowered toxicity to for example mammals and fishes, and can be safely used as pesticides.

Also, the compound (I) can be used as mixtures by formulating a herbicide containing the compound (I) with other kinds of herbicides, plant growth regulators, fungicides (e.g., organic chloride-based fungicides, organic sulfur-based fungicides, antibiotics, etc.), insecticides (e.g., organic phosphorus insecticides, naturally occuring insecticides, etc.), acaricides nematocides, synergists, attractants, repellants, coloring matters, fertilizers, etc. And the compound (I) can be used as a material for producing 3-mercapto or -unsubstituted thio-hexahydro-1H-isoinsodole-1-one, e.g., 2-(4-chloro-2-fluorophenyl)-2,3,4,5,6,7-hexahydro-3-methyldithio-1H-isoindole-1-one, having strong herbicidal activity.

Described in the following are the reference examples, examples and test examples to illustrate the content of this invention in detail.

REFERENCE EXAMPLE 1

4'-Chloro-2'-fluoro-2'-morpholino-2-cyclohexene-1-thiocarboxanilide

In 400 ml of chloroform was dissolved 78.9 g of 4-chloro-2-fluorophenylisothiocyanate, and 68.6 g of 1-morpholino1-cyclohexene was added dropwise to the solution with stirring over a 10-minute period. After stirring at room temperature for 10 hours, the reaction mixture was concentrated under reduced pressure, and the residue was treated with a small amount of cold ethanol. The resulting crystals were collected by filtration, and there was obtained 127.9 g of the subject compound (yield of 86%) as white crystals, m.p. 86°–88° C.

REFERENCE EXAMPLE 2

4'-Chloro-2'-fluoro-2-oxycyclohexane-1-thio-carboxanilide

In 800 ml of dichloromethane was dissolved 88.9 g of 4'-chloro-2'-fluoro-2-morpholino-2-cyclohexene-1-thiocarboxanilide.

The solution was washed twice with dilute hydrochloric acid and once with water, and dried over anhydrous sodium sulfate. The dichloromethane was distilled off under reduced pressure, thereby affording 61.7 g (yield of 81%) of the subject compound in crystals. Recrystallization from hexane yielded slightly yellow crystals, m.p. 97°–98° C.

REFERENCE EXAMPLE 3

4'-Bromo-2'-fluoro-2-oxocyclohexane-1-thiocarboxanilide

In 750 ml of chloroform was dissolved 158.3 g of 4-bromo-2-fluorophenylisothiocyanate, and 114.0 g of 1-morpholino-1-cyclohexane was added dropwise to the solution with stirring over a 10 minute period. After stirring was continued at room temperature for 5 hours, the reaction mixture was allowed to stand overnight and concentrated under reduced pressure. The residue was purified by column chromatography with the use of silica gel (developing solvent of dichloromethane), and there was obtained 158.2 g (yield of 70%) of the subject compound in crystals. Recrystallization from ethanol-hexane yielded slightly yellow crystals, m.p. 94°–95° C.

REFERENCE EXAMPLE 4

2-(4-Chloro-2-fluorophenyl)-3-hydroxy-2,3,4,5,6,7-hexahydro-1H-isoindol-1-one In 400 ml of ethanol was dissolved 40.0 g of 2-(4-chloro-2-fluorophenyl)-2,3,4,5,6,7-hexahydro-1H-isindol-1,3-dione, and 2.4 g of sodium borohydride was added to the solution with stirring over a 30-minute period, while cooling was effected suitably so as to maintain the reaction temperature at 20° to 30° C. After stirring was further continued at room temperature for 1 hour, the reaction mixture was neutralized with dilute acetic acid and concentrated to about one third of the original volume, followed by cooling. The resulting crystals were collected by filtration, washed with water and dried, thereby affording 36.2 g (yield of 90%) of the subject compound. Recrystallization from ethyl acetate yielded white crystals, m.p. 178°–179° C.

REFERENCE EXAMPLE 5

3-Chloro-2-(4-chloro-2-fluorophenyl)-2,3,4,5,6,7-hexahydro-1H-isoindol-1-one In 30 ml of dichloromethane was suspended 21.0 g of 2-(4-chloro-2-fluorophenyl)-3-hydroxy-2,3,4,5,6,7-hexahydro-1H-isoindol-1-one, and 7.5 ml of thionyl chloride was added to the suspension with stirring over a 20-minute period. The reaction solution was warmed, stirred at 40° to 45° C. for 1 hour and concentrated to dryness under reduced pressure. The residue was dissolved in methylene chloride, and the insoluble matter resulting from the addition of hexane was filtered out. The filtrate was concentrated to dryness under reduced pressure, thereby producing 19.5 g (yield of 87%) of the subject compound as crystals. Recrystallization from cyclohexane yielded white crystals, m.p. 89°–90° C.

EXAMPLE 1

2-(4-Chloro-2-fluorophenyl)-3a-hydroxy-3-imino-octahydroisoindole-1-thione

In 210 ml of ethanol were dissolved 4'-chloro-2'-fluoro-2-oxo-cyclohexane-1-thiocarbonilide and 9.3 g of acetone cyanhydrin, and 5 ml of 10% aqueous postassium carbonate solution was added, followed by stirring at room temperature for 5 hours. After cooling, the resulting crystals were collected by filtration, washed with dilute ethanol and dried, thereby producing 27.4 g (yield of 77%) of the subject compound in yellow crystals. m.p. 61°–62° C. (containing 1 mol of ethanol of crystallization).

EXAMPLE 2

2-(4-Chloro-2-fluorophenyl)-3a-hydroxy-1-thioxo-octahydroisoindol-3-one

In 220 ml of ethanol was suspended 25.0 g of 2-(4-chloro-2-fluorophenyl)-3a-hydroxy-3-imino-octahydroisoindol-1-thione and 20 ml of concentrated hydrochloric acid was added to the suspension, followed by stirring at 50° to 60° C. for several minutes. After cooling, 200 ml of water was added to the mixture, and the resulting crystals were collected by filtration, washed with 50% ethanol and dried, thereby producing 20.8 g (yield of 83%) of the subject compound. Recrystallization from ethanol yielded slightly yellow crystals, m.p. 156°–157° C.

EXAMPLE 3

2-(4-Bromo-2-fluorophenyl)-3a-hydroxy-1-thioxo-octahydroisoindol-3-one

In 350 ml of ethanol was dissolved 33.0 g of 4'-bromo-2'-fluoro-2-oxocyclohexane-1-thiocarboxanilide, and a solution of 7.0 g of potassium cyanide in 35 ml of water was added to the solution with stirring at room temperature over a 10-minute period, followed by adding 9.2 ml of concentrated hydrochloric acid at 10° to 20° C. over a 1 hour period, while cooling. After stirring was continued at room temperature for 1 hour, 30 ml of concentrated hydrochloric acid and 30 ml of water were added to the reaction mixture, and the mixture was warmed and stirred at 50° to 60° C. for 10 minutes. Upon cooling, there resulted crystals, which were collected by filtration, washed with dilute ethanol and dried, thereby producing 24.5 g (yield of 68%) of the subject compound. Recrystallization from ethanol yielded slightly yellow crystals, m.p. 163°–164° C.

EXAMPLE 4

2-(4-Chloro-2-fluorophenyl)-2,3,4,5,6,7-hexahydro-3-thioxo-1H-isoindol-1-one

Method a

In 75 ml of pyridine was dissolved 28.2 g of 2-(4-chloro-2-fluorophenyl)-3a-hydroxy-1-thioxo-octahydroisoindol-3-one, and 30 ml of acetic anhydride was added to the solution, followed by allowing to stand at room temperature overnight. The reaction mixture was concentrated under reduced pressure, and water was added to the residue. The resulting crystals were collected by filtration, washed with a small amount of cold ethanol and dried, thereby producing 24.8 g (yield of 93%) of the subject compound. Recrystallization from ethanol yielded red-purple crystals, m.p. 101°–102° C.

Method b

In 100 ml of acetone was dissolved 15.0 g of 3-chloro-2-(4-chloro-2-fluorophenyl)-2,3,4,5,6,7-hexahydro-1H-isoindol-1-one, and 10.0 g of sodium benzenethiolsulfonate was added to the solution, followed by stirring at room temperature for 2 hours. The resulting crystals were filtered out, and the filtrate was allowed to stand at room temperature overnight and concentrated under reduced pressure. The residue was dissolved in dichloromethane, and the solution was washed with aqueous sodium hydrogencarbonate solution, dried over anhydrous sodium sulfate and freed of the dichloromethane. The residue was purified by column chromatography with the use of silica gel (developing solvent of dichloromethane), thereby producing 13.1 g (yield of 89%) of the subject compound. Recrystallization from ethanol yielded red-purple crystals, m.p. 101°–102° C.

EXAMPLE 5

2-(4-Bromo-2-fluorophenyl)-2,3,4,5,6,7-hexahydro-3-thioxo-1H-isoindol-1-one

By the same procedure as described in Example 4, there was obtained the subject compound in red-purple crystals of 97° to 98° C. in melting point from 2-(4-bromo-2-fluorophenyl)-3a-hydroxy-1-thioxo-octahydroisoindol-3-one or 2-(4-bromo-2-fluorophenyl)-3-chloro-2,3,4,5,6,7-hexahydro-1H-isoindol-1-one.

EXAMPLE 6

A wettable powder was produced by mixing and pulverizing 30 parts of 2-(4-chloro-2-fluorophenyl)-2,3,4,5,6,7-hexahydro-3-thioxo-1H-isoindol-1-one, 5 parts of sodium ligninsulfonate, 5 parts of polyethylene glycol ether (Nonipol 85 ® Sanyo Chemical Industries, Japan) and 60 parts of clay.

EXAMPLE 7

A granule produced by adding water to a mixture consisting of 10 parts of 2-(4-bromo-2-fluorophenyl)-2,3,4,5,6,7-hexahydro-3-thioxo-1H-isoindol-1-one, 5 parts of sodium ligninsulfonate and 85 parts of bentonite, followed by kneading and granulating.

EXAMPLE 8

An emulsifiable concentrate containing 20 parts of 2-(4-chloro-2-fluorophenyl)-2,3,4,5,6,7-hexahydro-3-thioxo-1H-isoindol-1-one, 75 parts of xylene and 5 parts of polyethylene glycol ether (Nonipol 85 ® Sanyo Chemical Industries, Japan) was produced.

TEST EXAMPLE

Pots of 900 cm² made of plastics were filled with field soil, and sown with seeds of crab grass (*Digitaria adsendes Henr*), Pigweed (*Amaranthus retroflexus L.*) Lamb's-quarters (*Chenopodium album L. Var. centrorubrum, Makino*), Inutade (*Polygonum Blumei Meisn*), common purslane (*Portulaca oleracea L.*), Green foxtail (*Setaria viridis Beauv.*) corn, soybean and cotton, followed by covering 0.5 cm thick with soil. An emulsifiable concentrate containing the compound of the general formula (I) was diluted with water of 10 l so that the active ingredient (the compound (I)) might be at an application rate of 5, 10, and 20 g per are, respectively, and sprayed evenly over the soil surfaces by use of a spray gun. Three weeks later, investigation was carried out for the effect and phytotoxicity of each of the compounds used. The herbicidal effect is indicated by the following indices.

| Index | Effect | Inhibitory ratio (%) |
|---|---|---|
| 0 | None | 0 |
| 1 | Negligible | 0.1 to 50 |
| 2 | poor | 50.1 to 70 |
| 3 | medium | 70.1 to 87.5 |
| 4 | high | 87.6 to 99.9 |
| 5 | complete | 100 |

Phytotoxicity to crops is indicated by the following indices.

| Index | Phytotoxicity | Percentage of damage (%) |
|---|---|---|
| 0 | None | 0 |
| 1 | Negligible | 0.1 to 12.5 |
| 2 | Slight | 12.6 to 30.0 |
| 3 | Medium | 30.1 to 50.0 |
| 4 | Serious | 50.1 to 99.9 |
| 5 | Maximal | 100 |

The indices of phytotoxicity to crops, 0 and 1, denote the practical applicability to crops. The results are shown in the table.

TABLE

| Example No. | 4 | | | 5 | | |
|---|---|---|---|---|---|---|
| Application rate, g/a | 5 | 10 | 20 | 5 | 10 | 20 |
| Effect; | | | | | | |
| crab grass | 4 | 5 | 5 | 5 | 5 | 5 |
| pigweed | 5 | 5 | 5 | 5 | 5 | 5 |
| Lamb's-quarters | 4 | 5 | 5 | 5 | 5 | 5 |
| Inutade | 4 | 5 | 5 | 4 | 5 | 5 |
| Common purslane | 5 | 5 | 5 | 5 | 5 | 5 |
| Green foxtail | 4 | 4 | 5 | 4 | 5 | 5 |
| Phytotoxicity; | | | | | | |
| Corn | 2 | 2 | 2 | 1 | 1 | 2 |
| Soybean | 0 | 0 | 0 | 0 | 0 | 1 |
| Cotton | 0 | 0 | 1 | 0 | 1 | 1 |

I claim:
1. A compound represented by the formula

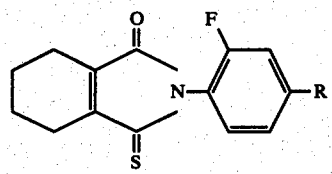

wherein R is halogen.

2. A compound as claimed in claim 1, wherein the halogen is chlorine.

3. A compound as claimed in claim 1, wherein the halogen is bromine.

4. A herbicidal composition comprising a herbicidally effective amount of at least one compound of claim 1 in combination with an inert carrier.

5. The herbicidal composition of claim 4 further comprising at least one member selected from the group consisting of emulsifiers, suspending agents, spreaders, penetrants, wetting agents, thickening agents or stabilizers.

6. A method of killing weeds comprising administering to said weeds the composition of claim 4.

7. The method of claim 6 wherein said composition is in the form of an emulsifiable concentrate, a wettable powder, a dust, a tablet, a spray or an ointment and said amount is between 10 and 90 weight percent.

8. The method of claim 6 wherein said composition is in the form of an oil-borne preparation and said amount is between 0.1 and 10 weight percent.

9. The method of claim 6 wherein said composition is in the form of granules and said amount is between 1 and 20 weight percent.

10. A method of preventing the emergence of weeds in a field comprising administering the composition of claim 4 to said field.

* * * * *